United States Patent
Szybek et al.

(10) Patent No.: US 11,397,151 B2
(45) Date of Patent: Jul. 26, 2022

(54) DEVICE AND A METHOD FOR MEASUREMENTS BY RAMAN SPECTROSCOPY

(71) Applicant: SERSTECH AB, Lund (SE)

(72) Inventors: Katja Szybek, Lund (SE); Peter Billsten, Veberöd (SE); Johan Diedrichs, Kävlinge (SE)

(73) Assignee: SERSTECH AB, Lund (SE)

( * ) Notice: Subject to any disclaimer, the term of this patent is extended or adjusted under 35 U.S.C. 154(b) by 0 days.

(21) Appl. No.: 17/618,925

(22) PCT Filed: Jun. 18, 2020

(86) PCT No.: PCT/SE2020/050634
§ 371 (c)(1),
(2) Date: Dec. 14, 2021

(87) PCT Pub. No.: WO2021/002790
PCT Pub. Date: Jan. 7, 2021

(65) Prior Publication Data
US 2022/0205921 A1    Jun. 30, 2022

(30) Foreign Application Priority Data
Jul. 1, 2019   (SE) .................................. 1930234-8

(51) Int. Cl.
*G01N 33/94*    (2006.01)
*G01N 21/65*    (2006.01)
*G01J 3/02*     (2006.01)
*G01J 3/44*     (2006.01)

(52) U.S. Cl.
CPC .......... *G01N 21/658* (2013.01); *G01J 3/0202* (2013.01); *G01J 3/0208* (2013.01);
(Continued)

(58) Field of Classification Search
CPC ............................ G01J 3/0202; G01N 21/658
See application file for complete search history.

(56) References Cited

U.S. PATENT DOCUMENTS

| | | |
|---|---|---|
| 7,113,265 B1 | 9/2006 | Sarrazin |
| 8,988,678 B2 | 3/2015 | Watson |

(Continued)

FOREIGN PATENT DOCUMENTS

| | | | |
|---|---|---|---|
| CN | 110132936 A | * | 8/2019 |
| CN | 112240881 A | * | 1/2021 |

(Continued)

OTHER PUBLICATIONS

Ocean Optics, " MMS Raman Spectrometer" 2006 (Year: 2006).*
(Continued)

*Primary Examiner* — Maurice C Smith
(74) *Attorney, Agent, or Firm* — Tucker Ellis LLP

(57) ABSTRACT

A device for detection of a substance by Raman spectroscopy comprises a holder (40) with an area (41) adapted for receiving a sample of the substance and a vibration engine (42). The vibration engine (42) is configured to move the holder (40) in a three-dimensional motion when the area (41) with the substance is arranged in front of a focusing lens (FL) of the spectrometer to provide a large actual sampling area and hence to achieve a strong signal at detection. The device comprises a SERS surface (30) arranged at the area (41) of the holder (40) for adsorption of the sample of the substance. A method for detection of a substance by use of the device is also presented.

15 Claims, 9 Drawing Sheets

(52) U.S. Cl.
CPC ............... *G01J 3/0272* (2013.01); *G01J 3/44* (2013.01); *G01N 33/94* (2013.01)

(56) References Cited

U.S. PATENT DOCUMENTS

| | | | |
|---|---|---|---|
| 10,883,873 B1 * | 1/2021 | Awadh | ................. G01J 3/0202 |
| 2010/0110423 A1 | 5/2010 | Villaumie | |
| 2018/0095025 A1 | 4/2018 | Hofmeister | |
| 2019/0049300 A1 | 2/2019 | Gu | |

FOREIGN PATENT DOCUMENTS

| | | | | |
|---|---|---|---|---|
| DE | 202012006556 U1 * | 12/2012 | ................. | G01J 3/44 |
| EP | 2546654 A2 | 1/2013 | | |
| JP | 2009103643 A * | 5/2009 | | |
| WO | WO-2019063745 A1 * | 4/2019 | ............. | G01N 21/03 |
| WO | WO-2021162327 A1 * | 8/2021 | ............. | G01N 11/16 |

OTHER PUBLICATIONS

B&W Tek, "Narcotics Testing with the TacticID Handheld Raman Analyzer", Jun. 23, 2015 (Year: 2015).*
CENTICE,"Installation and Operation Manual" Ocean Optics Inc, 2006.*
B&W Tek, "Narcotics Testing with the TacticID Handheld Raman Analyzer", Jun. 23, 2015.*
International Search Report and Written Opinion from corresponding International Application No. PCT/SE2020/050634, dated Jul. 17, 2020, 10 pages.

* cited by examiner

DEVICE AND A METHOD FOR MEASUREMENTS BY RAMAN SPECTROSCOPY

TECHNICAL FIELD

The present invention relates generally to the field of spectroscopy. More particularly, it relates to a device configured for measurements by a Raman spectroscopy system.

The invention also relates to a method for measurements by use of the device with a Raman spectroscopy system.

BACKGROUND OF THE INVENTION

Raman spectroscopy is a certain spectroscopy technique that enables observation of vibrational, rotational, and other low frequency modes in a system. Raman spectroscopy is common practice e.g. in the field of chemistry in order to provide a fingerprint by which different molecules may be identified.

Raman spectroscopy provides information about molecular vibrations that may be used for identification or quantification of a material which a sample is made up of. The sample is illuminated by an electromagnetic radiation source such as a laser or LED having monochromatic light. The light incident on the sample is scattered, absorbed or transmitted.

Raman spectroscopy is a well-established spectroscopic technique for rapid identifications of chemicals with high degree of accuracy. A material will give rise to a unique Raman spectrum, which makes the technique suitable for identifying materials.

The Raman effect occurs when a sample is illuminated by a monochromatic light which then interacts with vibrational modes of molecules in the sample.

Light scattered from the molecules gives rise to a vibrational spectrum that consists of a series of lines constituting a molecular "fingerprint".

The continued miniaturization of electronic components has furthermore led to the production of portable and handheld Raman instruments used for hand measurements of liquids, powders and solids. Such handheld instruments are suitable for in-field measurements, such as at incidents and accidents used by the police or for use by customs officers for on-site identifications of hazardous substances, drugs and other type of materials.

The optical module of Raman instruments generally consists of three main parts: an excitation source, e.g. typically a laser, a sampling device, e.g. an optical probe, and a spectrometer or detector. Optical probes typically deliver the laser radiation to the sample and transmit back-scattered Raman radiation from the sample to the spectrometer.

The Raman spectroscopy is based on inelastic scattering, i.e. the kinetic energy of an incident particle is not conserved, or on Raman scattering, i.e. the inelastic scattering of a photon. The scattering is induced by light in the form of a laser beam in the visible, near infrared, or near ultraviolet range.

Typically, a sample is illuminated with a laser beam having high focused laser power density. The electromagnetic radiation forms the illuminated spot on the sample. Backscattered light is collected to the spectrometer. Collected light is dispersed into wavelengths that are focused onto the detector.

SERS (Surface Enhanced Raman Spectroscopy) is a spectroscopic technique that allows sample identification at ultra-low volume concentration down to single-molecule scale.

SERS was first reported in 1974 by Fleischmann, Hendra and McQuillan who observed a strong Raman signal from pyridine molecules absorbed on a silver electrode. This discovery led to the development of Raman spectroscopic techniques that use SERS as a very sensitive and informative method with the enhancement factor in Raman signal up to $10^{14-15}$.

The SERS method is based on the fact that Raman signal from sample molecules absorbed on a nanostructured surface can be several orders of magnitude higher than the Raman signal from the same molecules without any SERS surface.

Commonly used SERS surfaces are gold (Au), silver (Ag) and copper (Cu) nanostructures applied on a silicon substrate with a roughened surface. Au and Ag are most often used because they are air stable, while Cu is more reactive. Ag nanostructures usually generate higher enhanced signals compared to signals from Au nanostructures, which has the same size and shape at both visible and NIR (Near Infra Red) laser excitation. SERS nanostructures range from nanorods to colloidal nanoparticles, and today there are many specially designed and commercially available SERS surfaces.

There are two factors that contribute to the enhancement of signals when using SERS surfaces; the increase in electromagnetic field, which is due to the localized surface plasmon resonance and which is theoretically calculated to about $10^{10}$-$10^{11}$, and the increase due to a chemical factor that is about $10^3$.

The use of SERS surfaces together with a handheld Raman instrument is disclosed in EP 2,546,654. The patent describes a method for detecting heroin in a composition and an apparatus used at the detection. A SERS surface is attached to a plastic spoon and is immerged into an alcoholic solvent containing the composition. The solvent will evaporate from the SERS surface while the heroin molecules will adsorb on the SERS surface. The spoon with heroine molecules on the SERS surface is manually hold by a user in front of the instrument and a focused laser spot of 100 μm is illuminating the SERS area.

EP 8,988,678 describes a solution to overcome tradeoff between spot size states and resolution which is based on a technology called Orbital Raster Scan (ORS). A Raman instrument includes an optical mirror as a special optical component. The mirror is operated to rotate by a rod connected to a piezo motor, which results in that the mirror moves a laser spot across a sample for scanning a larger sample area while the spectral resolution is maintained.

The Raman spectrometer sensitivity is related to the spot size and to the size of the sampling area. A small focus spot is desired to achieve high sensitivity, but this also reduces the size of the actual sampling area, which is an issue for non-uniform or non-homogenous samples. An example of such a sample is a tablet or capsule that comprises a pharmaceutical as the active substance and also a bulking agent or filler for distributing the active substance evenly within the tablet. Further, street drugs, such as cocaine and heroin, are often mixed with other substances for filling-up a delivery package, hence identification of included components by Raman spectroscopy can be difficult due to fluorescence from interferent components.

The high laser power density used in Raman spectroscopy provides problems. It is common to illuminate small areas of a sample in Raman spectroscopy and the high laser power density can lead to massive heat development which may severely damage the sample. Exposing the sample for a large amount of energy could also lead to other dangers, e.g. in the case of potentially explosive substances.

Another problem at detection of a substance when mixed with different components of a composition is that the characteristic spectra of the substance is hidden behind peaks from interfering components of the composition.

Accordingly, there is a need for an improved instrument that enables detection of substances by Raman spectroscopy.

SUMMARY OF THE INVENTION

An object of the present invention is to mitigate or eliminate one or more deficiencies and disadvantages of the prior art, such as the above-identified, singly or in any combination, by providing a device and a method according to the appended patent claims.

In a first aspect the invention relates to a device configured to provide improved measurements for detection of substances in pure states or as mixed compositions by Raman spectroscopy.

The device comprises a holder having an area adapted for receiving a sample of the substance and a vibration engine. The holder is configured to arrange the area for receiving the substance in front of a focusing lens of a spectrometer. The vibration engine is arranged to the holder and is configured to vibrate the holder in a three-dimensional motion to provide a large actual sampling area and hence to achieve a strong signal for detection of the substance.

According to an embodiment of the device the vibration engine is configured to move the holder in a vibratory motion. Further, according to another embodiment the vibration engine is configured to move the holder in a rotational motion or/and in a translational motion, such as the holder is rotated around an axis perpendicularly through the area and is translated along the axis perpendicular to the area at detection. Thus, the area, which is adapted for receiving a sample of the substance, follows the motion of rotation and translation resulting in that a large actual sampling area is provided with many hot spots, i.e. localized surface plasmon resonances, and in that a strong signal is achieved.

In general, a hot spot is a spot on a non-homogenous sample where a Raman signal is enhanced due to localized surface plasmon resonances in the SERS substrate, that comprises nanoparticles. The term hot spot is also used to describe regions of strong Raman signals in non-homogenous solid samples, e.g. pharmaceutical tablets.

Further, the spectrometer of the device according to a first embodiment is a hand-held Raman spectrometer having a nozzle for detection of the substance. The nozzle is protruding from the spectrometer, where the focusing lens is arranged at a distal end of the nozzle facing the area of the holder.

To further improve the measurements, the device comprises a SERS surface arranged at the area of the holder for adsorption of the sample of the substance.

According to an alternate embodiment, the device further comprises means for arrangement of a solid substance at the area of the holder, which is adapted for receiving a sample.

In a second aspect the invention relates to a method for use of the device to provide improved measurements with a Raman spectroscopy system.

The method for detection of a substance by Raman spectroscopy comprises a first step of providing a device, which comprises a holder with an area configured for receiving a sample of the substance and a vibration engine configured for vibrating the holder. The method comprises a second step of arranging a sample of the substance at the area, and a step of arranging the holder in front of a focusing lens of a spectrometer, wherein the area of the holder is facing the focusing lens of the spectrometer.

Further, the method comprises the step of starting the vibration engine by a control unit for moving the holder in a three-dimensional motion to provide a large actual sampling area and thus to achieve a strong signal. Thereafter a spectrometer is activated for detection mode.

According to a first embodiment, the spectrometer is a hand-held Raman spectrometer for detection of the substance.

To further improve the measurements, the method comprises a step of providing a SERS surface and arranging the SERS surface at the area of the holder, which is configured for receiving a sample.

The method further comprises the step of arranging a sample of the substance at the SERS surface.

Further, the method comprises the steps of providing a vial containing a solvent and adding a sample of the substance to the solvent, closing the vial with a cap and shaking the vial until the substance has dissolved and thereafter supplying a drop of the dissolved substance to the SERS surface.

The solvent is for example 2-propanol, or a mixture of acetonitrile and acetone.

The method is suitable for detection of heroin, which is a substance that is difficult to detect even in pure state since the Raman signal from heroin is weak and due to that fluorescence often appears. Further, heroin is generally mixed in a composition with different filler components, and hence difficult to detect since the heroin spectrum might be hidden by peaks from the filler components. Also, the method is suitable for detection of fentanyl, or other types of drugs belonging to the same category as heroin.

According to an alternate embodiment the method comprises the step of providing means for arrangement of a solid substance at the area of the holder.

Further objects, features and advantages of the present invention will appear from the following detailed description, the attached drawings and the appended claims.

BRIEF DESCRIPTION OF THE DRAWINGS

In order to explain the invention, embodiments of the invention will be described below with reference to the drawings, in which.

Same reference numerals have been used to indicate the same parts in the figures to increase the readability of the description and for the sake of clarity.

DESCRIPTION OF EMBODIMENTS OF THE INVENTION

Specific embodiments of the invention will now be described with reference to the accompanying drawings. This invention may be embodied in many different forms and should not be construed as limited to the embodiments set forth herein; these embodiments are provided so that this disclosure will be thorough and complete, and will fully convey the scope of the invention for those skilled in the art. The terminology used in the detailed description of the embodiments illustrated in the accompanying drawings is not intended to be limiting of the invention.

Figure 1:
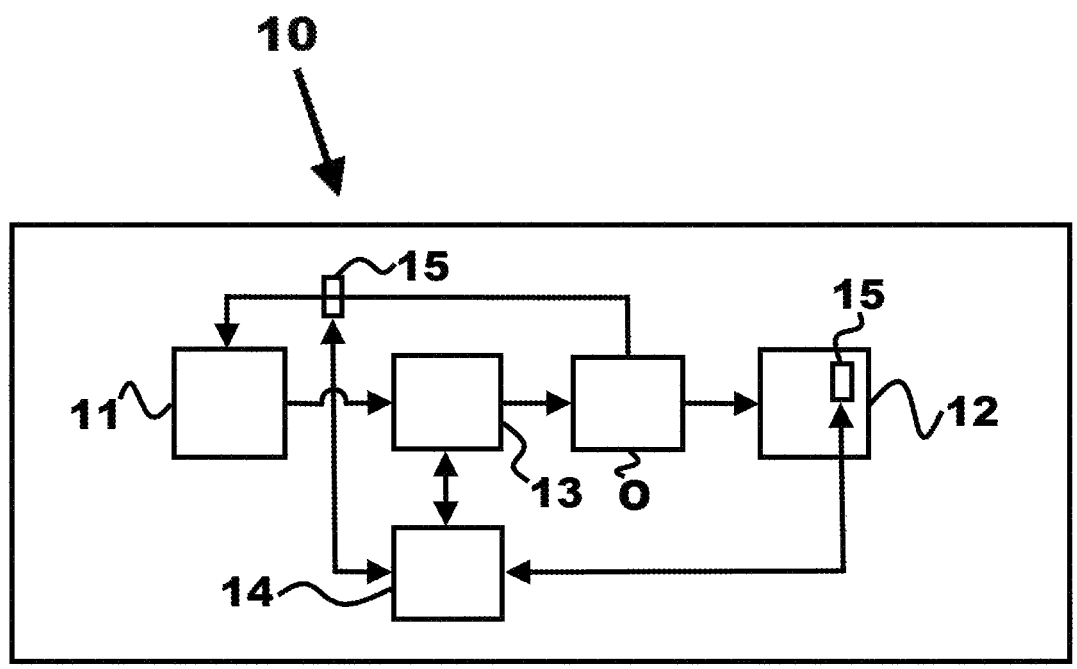
FIG. 1 is a schematic block diagram showing a spectroscopy system according to an embodiment.

FIG. 1 is a schematic block diagram illustrating a Raman spectroscopy system 10 for analysing inelastic scattered light from an object O. In this disclosure the terms sample and object may be used interchangeably unless explicitly stated otherwise. The system 10 comprises an electromagnetic radiation source 11, a spectrograph unit 12, a focusing lens 13, a control unit 14, and a detector 15.

The electromagnetic radiation source 11 emits electromagnetic radiation, e.g. light, passing through the lens 13. The focused light hits the sample and illuminates a spot of the sample resulting in a scattering of the light. The Raman spectroscopy system 10 is well-known within the art.

It should be noted that in the schematic system of FIG. 1, the solid arrows show how the electromagnetic radiation travels through the system, whereas the dashed lines show the signals sent from or received by the control unit 14. FIG. 1 should not be interpreted as showing the exact position of each component in the system. Hence, it should be noted that the spectrograph unit 12 may be positioned on the same side of the object as the lens assembly.

Figure 2:
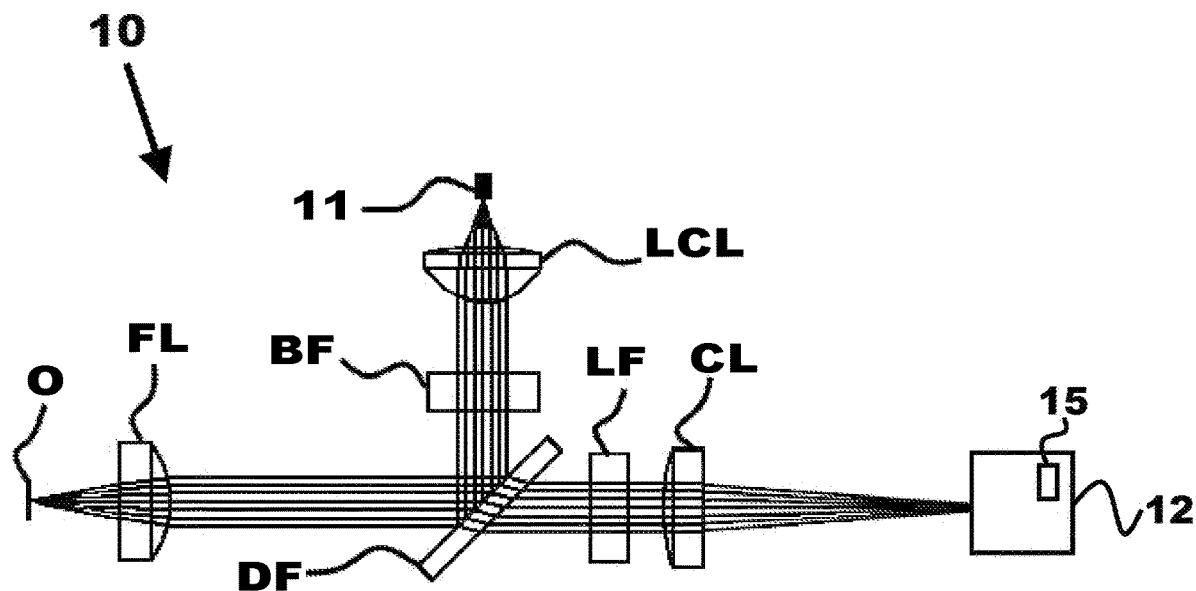
FIG. 2 is an optical setup of a Raman spectroscopy system, where a sample is arranged close to a focusing lens of the system.

FIG. 2 illustrates an optical setup of the Raman spectroscopy system 10, where an object O or a sample is arranged close to the focusing lens of the system 10.

A typical Raman system illuminates a sample with a focused laser light to produce a spot, which is common for the sample excitation and for the Raman scattering. Laser light from a laser diode is collimated through a laser collimation lens LCL and then propagates through a laser clean up filter CF and redirects 90° by a dichroic filter DF towards a sample. The laser beam is focused onto a tiny spot, typically <20 µm, on the sample by a focusing lens FL. Then the laser light interacts with the sample molecules and scatters Raman photons. Thereafter, the Raman light propagates trough the focusing lens FL, the dichroic filter DF and a long pass filter LF and is focused on an entrance slit to a spectrometer by an in-coupling lens IL.

The spot from the sample is magnified when it propagates towards the spectrometer. Due to the magnification, the spot focused on the slit is typically about 2,5 times larger than the spot on the sample.

The slit size is critical for the spectral resolution and varies typically between 10 and 200 µm. The narrow the slit, the higher optical resolution or ability to distinguish closely spaced peaks in the detected Raman spectrum. As the slit gets wider, the spectral resolution is impaired since the peaks become broader, i.e. the closely spaced peaks merge together into broader bands and the significant information about the spectrum may be lost.

On the other hand, the wider the slit, the better collection of light to the spectrometer, which will increase the system sensitivity. This states a well-known tradeoff between the spot size, optical resolution and the sensitivity in Raman systems.

Since a spot on the sample undergoes a magnification of about 2,5 times before it is focused on the slit, the spot on the sample needs to be quite tight originally to enable it to be collected through the narrow slit. However, a small laser spot will illuminate only a small fraction of the sample area resulting in that the sample component of interest could be more or less or completely missed. A large spot illuminates a larger sample area but requires a wider slit to collect more light, which leads to a loss in resolution.

A problem that arises from measurements using SERS surfaces is that a non-uniform distribution of molecules is adsorbed on the SERS surface. The surface plasmon resonance is localized at some specific hot spots on the surface, where the molecules are trapped or adsorbed due to the roughened surface where the signal is produced. In order to cover many of these hot spots and increase the probability to get an enhanced signal, the laser spot size on the surface should typically be 100 µm or more.

Figure 3:
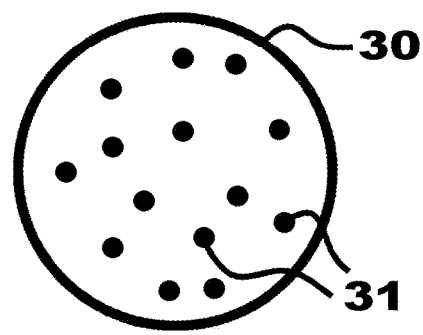
FIG. 3 shows a front view of a SERS surface with non-uniform distributed hot spots, where molecules from a sample are trapped.

FIG. 3 illustrates a front view of a SERS surface 30 with non-uniform distributed hot spots 31, i.e. localized surface plasmon resonances, where molecules from a sample are trapped.

An object of the present invention is to provide a device for improved measurements at detection of substances by Raman spectroscopy.

A device according to the invention comprises a holder 40 with an area 41 arranged at a front side of the holder 40, where the area 41 is adapted for receiving a sample of the substance to be detected. The holder 40 is configured to arrange the area 41 in front of a focusing lens FL of a spectrometer.

The device further comprises a vibration engine 42, which is adapted to be arranged to the holder 40. The vibration engine 42 is configured to vibrate the holder 40 in a three-dimensional motion around an axis perpendicularly through the area 41 for providing a large actual sampling area and to cover as many hot spots as possible, and hence to achieve a strong signal for detection of the substance.

The vibration engine 42 is for example a low-cost, commercially available motor, typically used in mobile cellphones and is powered with a power source 44, such as a battery.

According to an embodiment, the device comprises a SERS surface 30 arranged at the area 41 of the holder 40 for adsorption of a sample of the substance.

Further, the device comprises a Raman spectrometer for detection of a substance, for example a hand-held spectrometer, which also is denoted as the instrument below. A nozzle 43 is protruding from the spectrometer, where the focusing lens FL is arranged at a distal end 46 of the nozzle 43 facing the area 41 of the holder 40.

Figure 4:
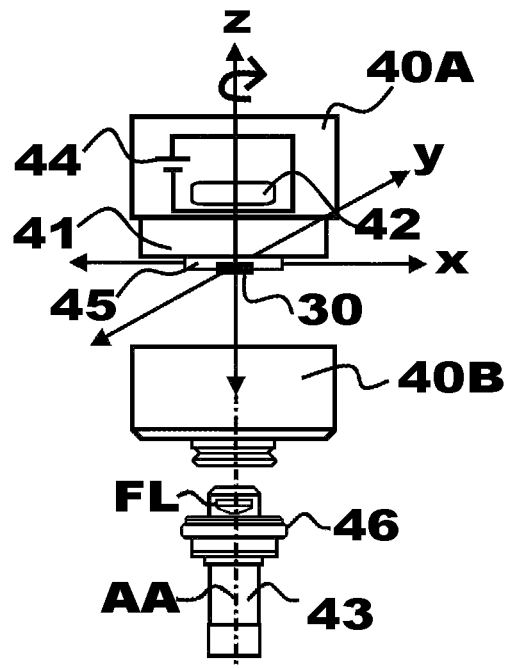
FIG. 4 illustrates an exploded view of a holder having a first holder part and a second holder part arranged in front of a nozzle of a spectrometer.

FIG. 4 illustrates an exploded view of the holder 40 according to a first embodiment having a first holder part 40A and a second holder part 40B arranged in front of a nozzle 43 of the spectrometer. A SERS surface 30 is attached to a disk 45, which is arranged to the area 41 of the first holder part 40A. The optical axis AA of the spectrometer is synchronized with the axis perpendicularly to the area 41 in a static state, i.e. when the vibration engine is not activated.

The two parts 40A, 40B of the holder 40 are configured to be arranged as a unit in abutment with each other. The second holder part 40B is configured to be arranged to the nozzle 43 and to embed the focusing lens, hence protecting it. The disk 45 and the area 41 could for example be made of a magnetic material for providing an easy and secure arrangement of the SERS surface to the area 41.

According to an alternate embodiment, the holder 40 could be designed differently, such as having means for arrangement of a solid sample or a container with a sample to the area 41.

Further, the device comprises a control unit (not shown) configured to operate the vibration engine 42. The provided motion of the holder 40 has several degrees of freedom; translation in x-, y- and z-direction, clockwise and counter-clockwise rotations and vibrations along the z-axis.

The vibration engine puts the holder 40 with the area 41 into vibrations in such way that rotations and translations are induced, resulting in that the area 41 with the sample is moved simultaneously several millimeters in x- and y-direction and several micrometers in z-direction. The axis of the holder 40 defines the z-direction, which also is aligned with the optical axis AA of the spectrometer. When the vibration engine is activated, the rotations are off axis due to the total motion resulting in that the size of the actual sampling area is enlarged. The motion of the holder 40 along the optical z-axis provides a slightly defocus of the laser beam from the spectrometer, which will be explained in detail below.

Figure 5:
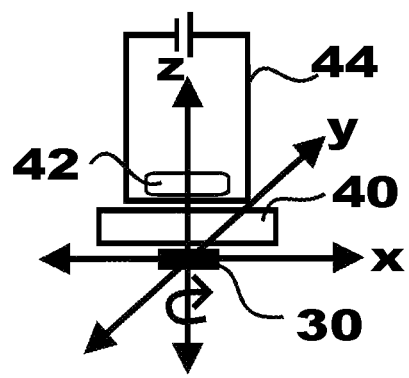
FIG. 5 is a view illustrating the movement of the device with the vibration engine arranged thereto, wherein the device is vibrated resulting in translations and rotations in relation to an x-axis, a y-axis and a z-axis.

FIG. 5 is a view illustrating the movement of the holder 40 of the device when the vibration engine 42 is arranged to the holder 40. The holder 40 with a SERS surface 30 attached to the area 41 of the holder part 40A is vibrated resulting in translations and rotations in relation to an x-axis, a y-axis and a z-axis.

Since rotational, translational and vibratory movements occur simultaneously, the analyzed area is further increased, i.e. the starting point and the end point at measurements of the sample will not be the same. Analogous, the vibration will not be provided between two specific end points in the sample, since the rotational and translational motions continuously moves to new sample regions.

According to an alternate embodiment, the device comprises an exchangeable vial for arrangement of a fluid substance at the area of the holder.

Tests have been performed to show the improvement of measurements using the inventive device at detection of substances by Raman spectroscopy. A main goal with the tests was to provide a larger actual sampling area, wherein more hot spots 31 are covered while a high resolution is maintained resulting in a strong signal from a sample of the substance of interest.

A hand-held instrument was used for the tests, which has a similar construction as the spectrometer showed in FIG. 2 and with a nose adapter or a nozzle 43 protruding from the spectrometer.

Figure 6:
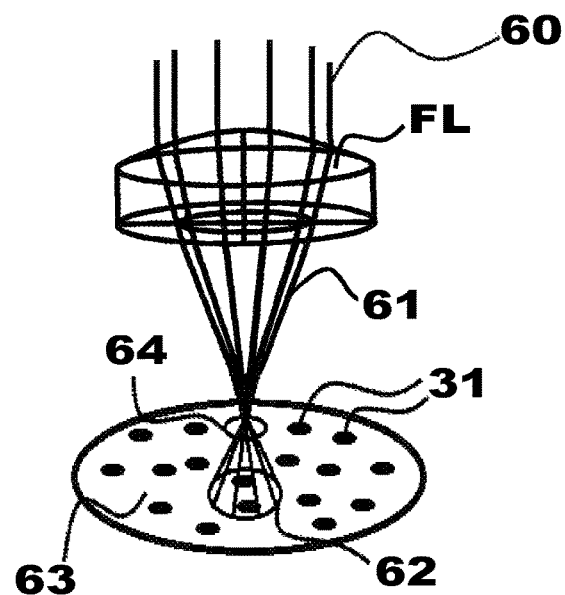
FIG. 6 is a perspective side view showing radiation from a laser beam of a Raman instrument that enters the focusing lens and creates a focused beam and a defocused beam, respectively, hence hitting one hot spot or more hot spots of a target surface.

FIG. 6 is a perspective side view illustrating radiation from a laser beam 60 of a Raman instrument, which enters the focusing lens FL. A focused laser beam 61 and a defocused laser beam 62 are created, respectively, which are hitting one hot spot 31 or more hot spots 31 of a target surface 63. The laser beam that incidents towards the focusing lens FL is a collimated Gaussian beam with approximately a flat wavefront. When passing the focusing lens FL, the laser beam 60 starts to converge to a beam focus 64. At the beam focus the wavefront is planar again, and the laser beam has a Gaussian profile where the spot radius is the distance from the intensity maximum of the laser beam to a point where the intensity of the laser beam drops to $1/e^2$, i.e. 13.5% of the intensity maximum. After the beam focus 64, the laser beam diverges and the wavefront curvature changes in the opposite direction.

A beam diameter at a beam focus 64 is less than about 20 μm, which can result in that the laser beam completely misses the hotspots 31 on the SERS surface 30. In order to increase the probability to cover hotspots 31, the beam must be defocused by displacing the SERS surface 30 several hundred micrometers away from the beam focus 64 along the optical axis. This results in a decrease in beam intensity as well as in wavefront aberrations, but an increase of the spectral area.

Figure 7:
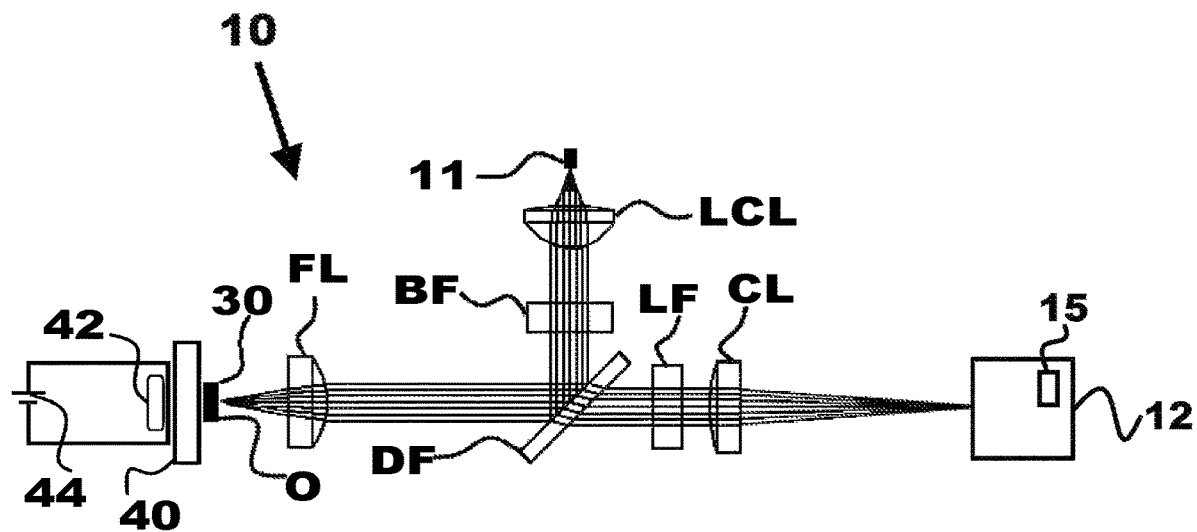
FIG. 7 is the Raman spectroscopy system of FIG. 2, where a holder with a SERS surface is arranged in front of a focusing lens of the system and where a vibration engine is arranged at the holder.

FIG. 7 shows the Raman spectroscopy system 10 of FIG. 2, where a holder 40 with a SERS surface 30 is arranged in front of a focusing lens FL of the system 10 and with the vibration engine 42 arranged to the holder 40.

To further show the improvement of the measurements when using the device according to the invention, a SERS surface 30 was used in the tests. The size of a SERS surface 30 can be chosen optionally, for example being 3×3 cm or 4×4 cm, and has a thickness of about 0.6 mm. The preparation of the sample for use with the SERS sample preparation starts by providing an exchangeable plastic vial or container having a resealable cap, which was filled with a solvent. The solvent is for example a mixture of acetonitrile and acetone or a mixture of acetonitrile and 2-propanol or a methanol.

Then a small amount of heroin powder was added to the solvent. The concentration of heroin can range between 0.3 mg/μl or higher. The cap was attached, and the container was shaken until the sample of heroin was dissolved.

The SERS surface 30 was arranged to the area of the holder 40 of the device. A drop of the heroin solution in the container was added directly on the SERS surface. After a short period of time the solvent of the sample was evaporated and the SERS surface 30 was dry.

Firstly, a static test was performed wherein a SERS surface 30 was used to get a first spectrum of the heroin sample. The SERS surface 30 with a sample of the substance was placed at the focal distance of the focus lens FL, which is mounted inside the nose adapter or nozzle 43 of the instrument, and a detection of the sample was made.

Then, the vibration engine 42 was arranged to the holder 40 and was activated. Thus, the holder 40 with the SERS surface 30 and the heroin sample was put in vibration, wherein both a translation and a rotation were provided. The sample surface was moved simultaneously several hundred μm in a three-dimensional motion, resulting in a movement of several degrees in relation to the relatively laser focal point from the Raman instrument. Hence, the laser was interacting with a large actual sampling area and the probability to cover more of plasmon hot spots increased.

Figure 8:
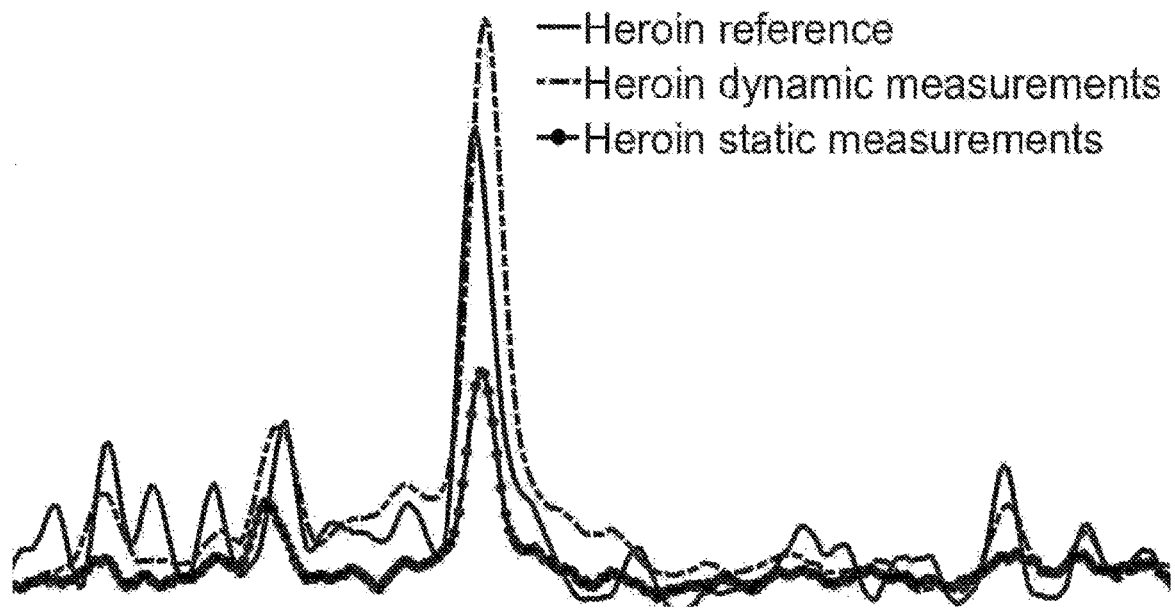
FIG. 8 is a diagram showing static and dynamic measurements of heroin molecules adsorbed on a SERS surface in comparison with a reference spectrum.
Figure 9:
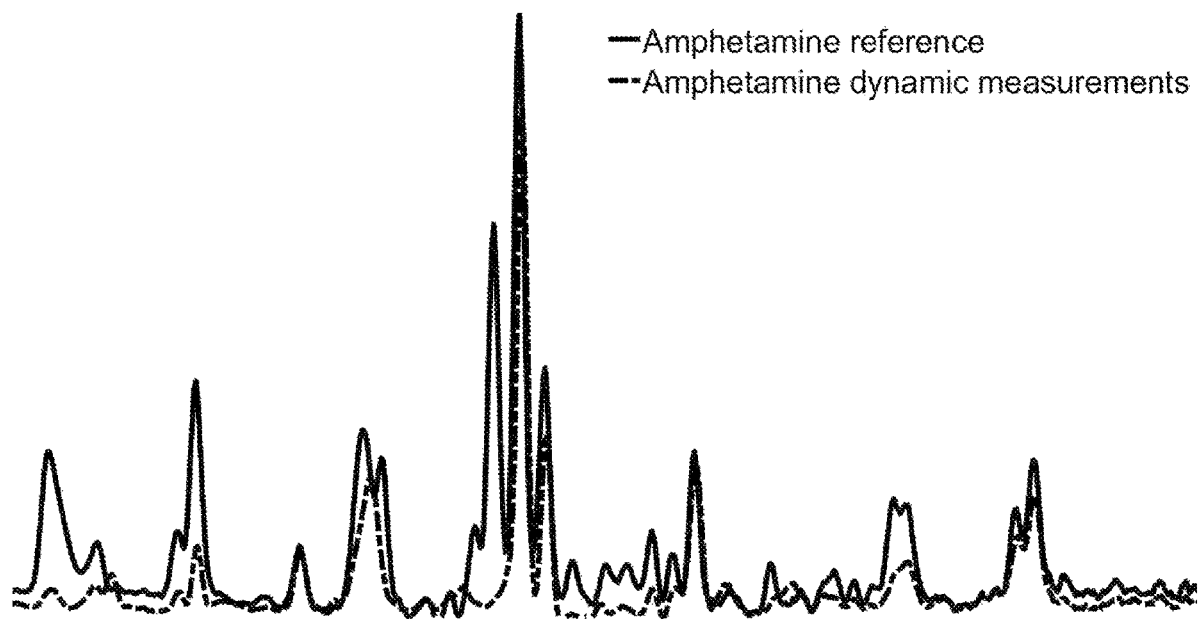
FIG. 9-FIG. 15 are diagrams showing dynamic measurements of different narcotic substances of which molecules are adsorbed on a SERS surface in comparison with a reference spectrum.
Figure 10:
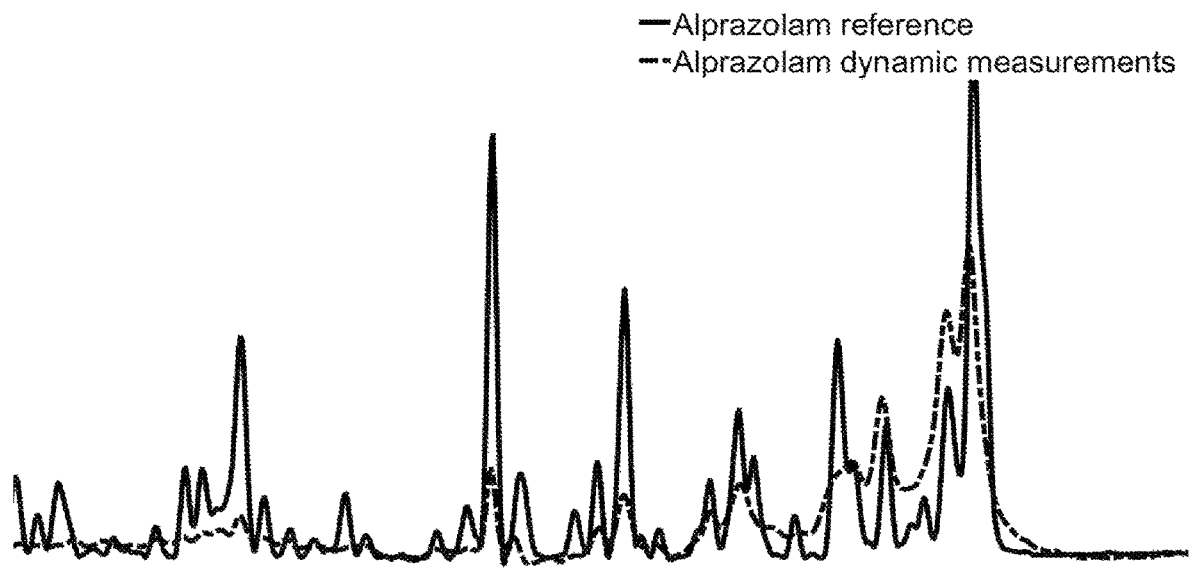
Figure 11:
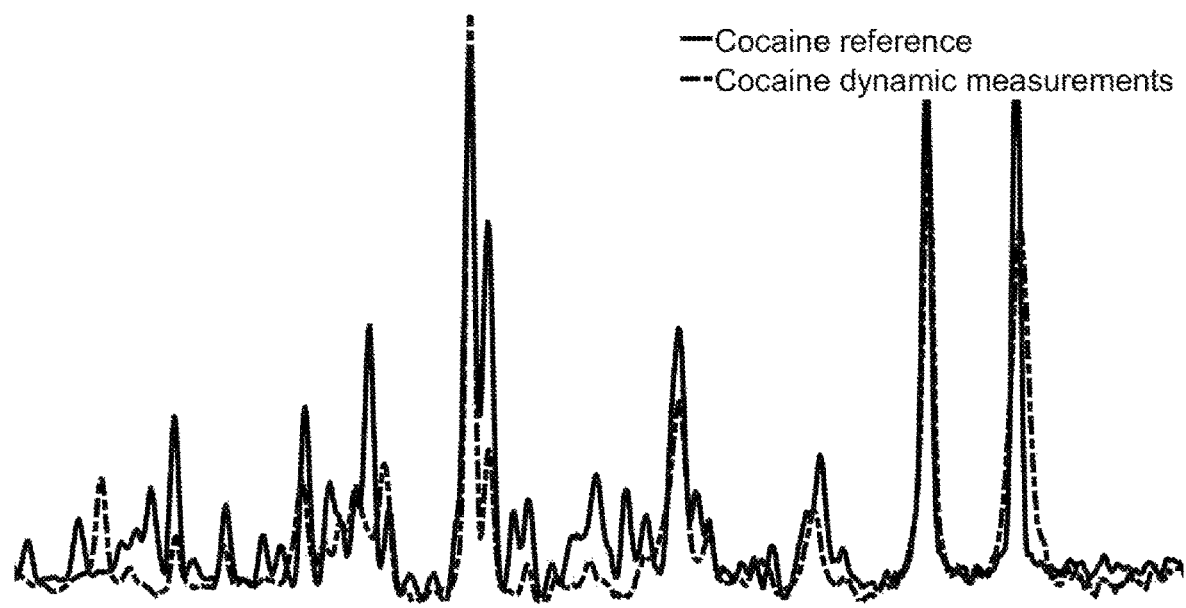
Figure 12:
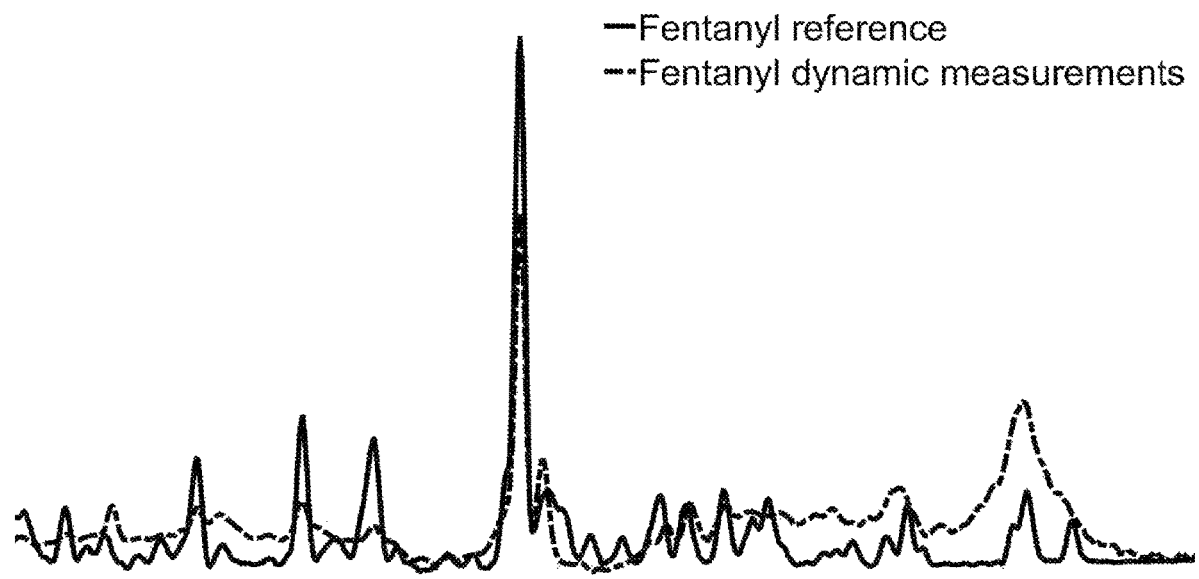
Figure 13:
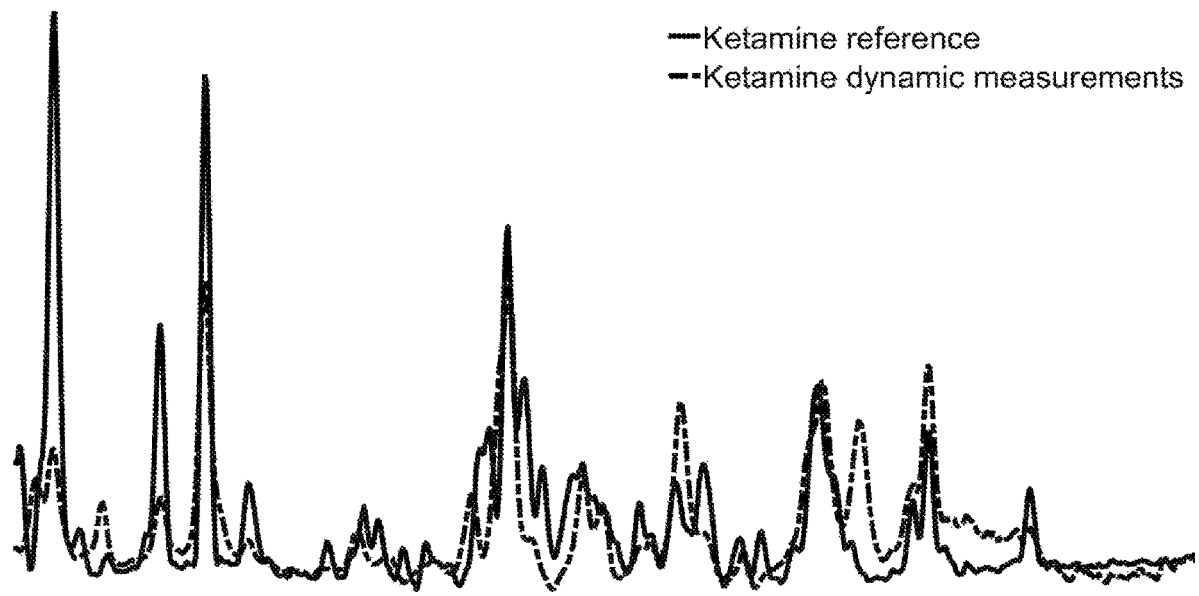
Figure 14:
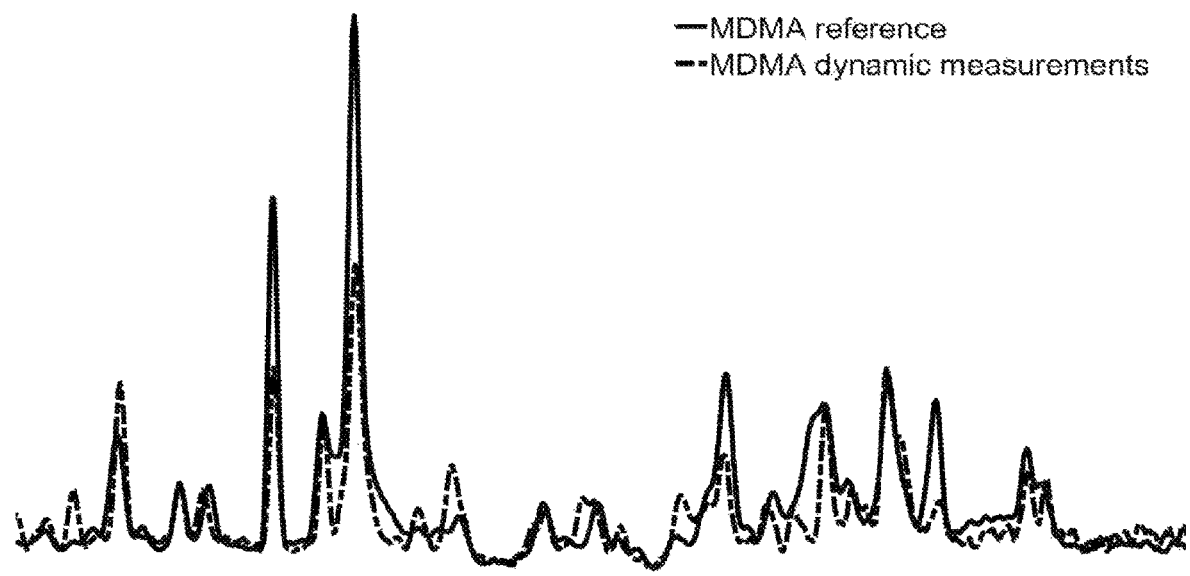
Figure 15:
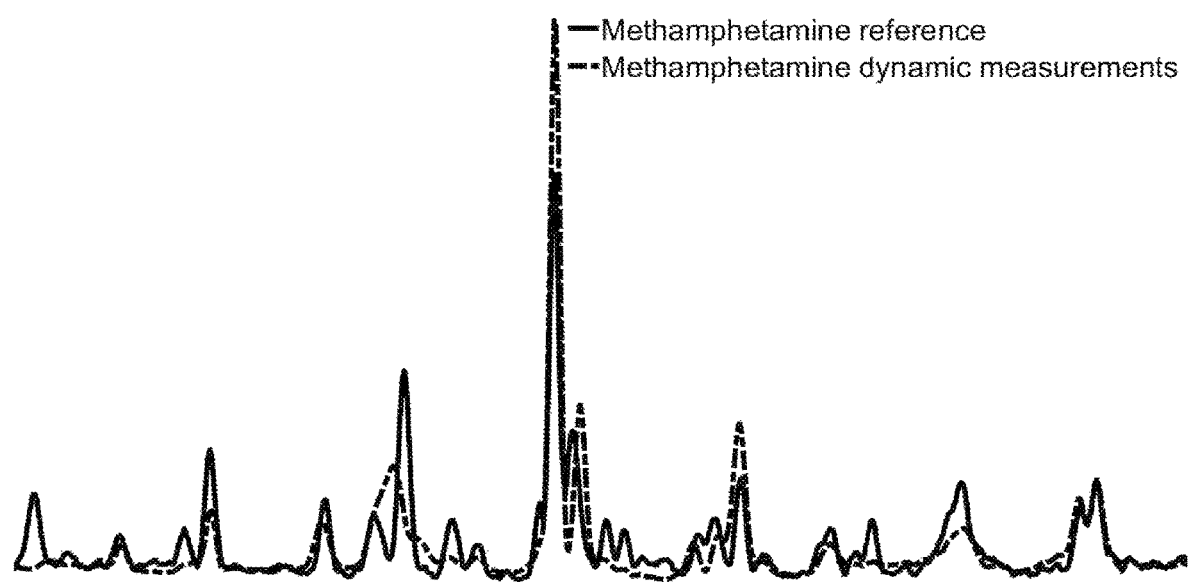

FIG. 8 shows spectra from the tests in comparison with a reference spectrum, wherein static and dynamic measurements of heroin molecules adsorbed on a SERS surface 30 were performed. This experiment showed that the intensity of the observed Raman signal due to the dynamic measurement with the vibration engine 42 increased with approximately 50% compared to the static measurement.

In summary, instead of defocusing the laser beam and still be able to cover more hot spots 31 with a focused beam, the SERS surface with the sample 30 can be put into motion during the measurements while exposed to the laser light.

The inventors have shown that by providing a three-dimensional motion to a sample on a SERS surface 30 for detection by Raman spectroscopy, several hot spots 31 can be covered without defocusing the laser beam and with the beam intensity maintained, resulting in achievement of an enhanced strong signal for detection.

FIG. 9-FIG. 15 show static and dynamic measurements of different narcotic substances of which molecules are adsorbed on a SERS surface in comparison with a reference spectrum. The inventors have performed tests to verify the importance of use a SERS-surface according to the invention to improve the Raman signal and to make it possible to measure and identify drugs in a variety of samples.

The inventive idea of using SERS-surfaces with Raman spectroscopy was firstly chosen to apply the technology in measurements of heroin, since there are existing problems with Raman and heroin. Heroin is a relatively weak Raman scatterer, and the Raman signal from heroin is often combined with disturbing fluorescence. In addition, heroin is usually mixed with various substances that increase the fluorescence problem and dilute the heroin, resulting in a lower intensity of the heroin Raman signal from the analysed sample.

Further, the inventors have found in tests that there are several substances that will benefit from enhancement by use of SERS-surfaces in measurements with Raman spectroscopy. The inventive method will provide possibilities to measure low concentrations of substances, for example down to levels where narcotics can be detected in urine. Some examples of drugs are disclosed below.

Fentanyl is a very potent substances that act on the same receptors as morphine and heroin. For this reason, it is a drug that can be used instead of morphine or heroin, or to dilute heroin, while the drug effect is maintained. The potency of fentanyl is approximately 50 times stronger than the potency of heroin, hence fentanyl in street samples are highly diluted. In addition, there are some types of fentanyl that are about 100 times more potent than regular fentanyl. For this reason, these substances are usually heavily diluted and thus hard to identify in measurements without enhancing the Raman signal. Enhancement of the Raman signal by means of the SERS technology according to the invention has been shown to improve the ability to identify Fentanyl.

Alprazolam is a pharmaceutical substance that is used in treatment of patients with anxiety. These pills are frequently found at the illegal market. The drug load in a pill containing alprazolam is in the range of 0.25 mg to 2 mg. The low concentration makes it hard to identify alprazolam and enhancement of the Raman signal at measurements by use of the inventive method improves the interpretation.

MDMA (i.e. ecstasy) is usually found in colourful, homemade pills. In many cases the colour pigments give rise to disturbing fluorescence that may hinder the identification of the substance. By applying the SERS technology at measurements of ecstasy tablets, it is possible to quench some of the fluorescence simultaneously as the Raman signal is increased to improve the quality of the obtained Raman spectrum.

The substance mescaline has some inherent fluorescence that lowers the ability to obtain a spectrum with enough quality to identify this substance. In addition, the origin of mescaline is the peyote cactus and there can be additional disturbance from fluorescent biomolecules. It is thus, an advantage to use the SERS technology according to the invention at measurements to circumvent the disturbances mentioned above.

Cocaine HCl is easily identified in standard Raman measurements. However, the presence of cocaine in contraband can be masked by mixing the drug with charcoal that turns the white powder black. Black samples are generally difficult to identify with Raman spectroscopy, but use of SERS-surfaces according to the invention will make it is possible to identify the presence of cocaine.

The Raman signature of amphetamine is quite clear, but there are limitations to identify this drug in bulk measurements of mixtures. The inventive method improves the detection of Amphetamine when the drug is mixed with substances that disturb the identification. Also, the use of SERS-surfaces will increase the sensitivity resulting in that low concentration formulations can be analysed and identified.

Figure 16A:
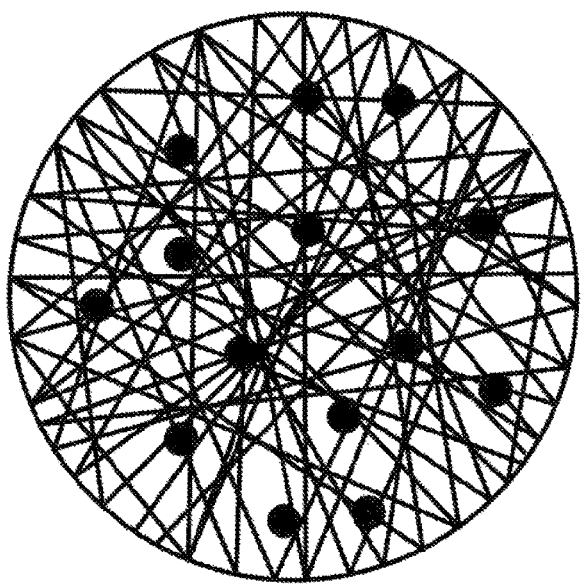
FIG. 16A-16C are views illustrating the increase in spectral area of a SERS surface at vibration of the device.
Figure 16B:
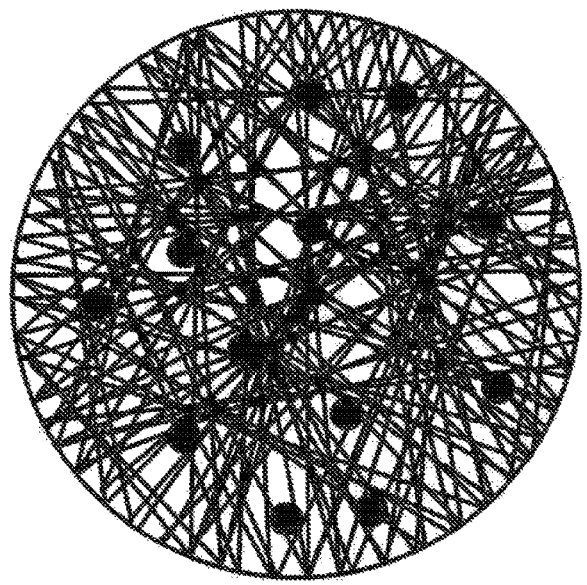
Figure 16C:
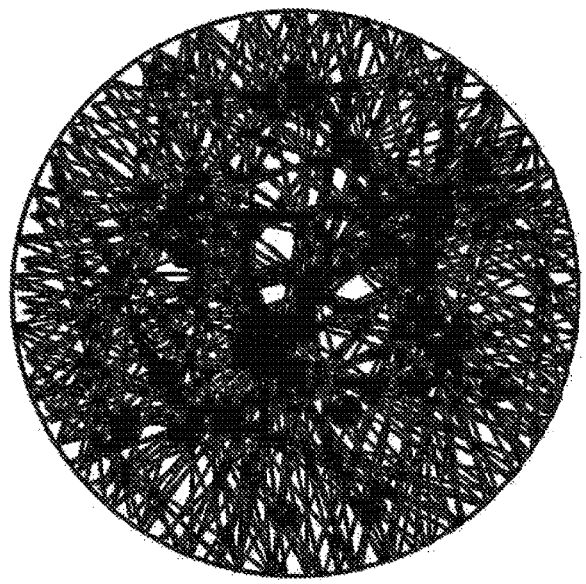

FIG. 16A-16C are views illustrating the increase in spectral area of a SERS surface 30 with a sample arranged to the holder 40 that is vibrating. These illustrations are theoretical simulations, wherein the rotation is 25 degrees in FIG. 16A, 75 degrees in FIG. 16B and 100 degrees in FIG. 16C. As the laser beam interacts with a large spectral area when the sample is vibrating, the probability increases to cover several hotspots 31 with the focused spot, resulting in an enhanced and strong signal from the substance at detection.

A second object of the invention is to provide a method for improved measurements at detection of a substance by Raman spectroscopy. The method is initiated by a step of providing a device, which comprises a holder 40 with an area 41 configured for receiving a sample of the substance and a vibration engine 42 configured for vibrating the holder 40. Then a sample of the substance is arranged at the area 41 of the holder 40, thereafter the holder 40 is arranged in front of a focusing lens of a spectrometer, where the area 41 of the holder 40 is facing the focusing lens FL. The vibration engine 42 is then started in a next step by a control unit for moving the holder 40 in a three-dimensional motion, and a spectrometer is activated for detection mode. It should be noted that the motion can be set by the control unit, e. g. the rate of the vibration, the direction and the frequency of rotation and translation. The spectrometer is a Raman spectrometer, preferably a hand-held instrument.

To further improve the measurements, a SERS surface 30 is provided, and the sample of the substance is arranged to the SERS surface, which then is arranged to the area 41 of the holder 40. The steps of the method as described above are then initiated.

Further, the method comprises the steps of providing a vial containing a solvent, adding a sample of the substance to the solvent, closing the vial with a cap and shaking the vial until the substance has dissolved, and supplying a drop of the dissolved substance to the SERS surface 30. The solvent can for example be a mixture of acetonitrile and acetone, or 2-propanol.

Further, the method is suitable for detection of heroin as the substance of interest, where a sample of the heroin substance is dissolved in a solvent and then a drop thereof is added to a SERS surface 30 and arranged to the area 41 of the holder 40.

According to an alternate embodiment, the method further comprises a step of providing means for arrangement of a solid substance at the area 41 of the holder 40. According to another alternate embodiment, the method further comprises the step of providing a vial for arrangement of a fluid substance at the area of the holder.

The inventive device and the method are specifically useful in critical situations such as at accidents or in customs office for facilitate rapid and exact measurements to detect toxic or prohibited substances.

The description above shall be considered as an exemplification of the principles of the invention and are not intended to limit the invention to the specific embodiments as illustrated. Other embodiments than the ones described can exist within the scope of protection, for example an alternative embodiment of the device can have the SERS surface arranged to a magnetic means for attachment with a single click to a holder 40 made of metallic material.

It should be emphasized that the term "comprise/comprising" when used in this specification is taken to specify the presence of stated features, integers, steps, or components, but does not exclude the presence or additions of one or more other features, other elements or steps. Reference signs in the claims are provided as clarifying examples and shall not be construed as limiting the scope in any way.

The invention claimed is:

1. A device for detection of a substance by Raman spectroscopy, the device comprising:
    a holder having an area adapted for receiving a sample of the substance, wherein the holder is configured to arrange the area in front of a focusing lens of a spectrometer;
    a SERS surface arranged at the area of the holder for adsorption of the sample of the substance; and
    a vibration engine arranged to the holder, wherein the vibration engine is configured to move the holder in a three-dimensional motion to provide a large sampling area and hence to achieve a strong signal for detection of the substance, and wherein the holder is rotated around an axis perpendicularly through the area and is translated along the axis.

2. The device of claim 1, wherein the vibration engine is configured to move the holder in a vibratory motion.

3. The device of claim 1, wherein the vibration engine is configured to move the holder in a rotational motion.

4. The device of claim 1, wherein the vibration engine is configured to move the holder in a translational motion.

5. The device of claim 1, comprising a nozzle protruding from the spectrometer, where the focusing lens is arranged at a distal end of the nozzle facing the area of the holder.

6. The device of claim 1, comprising a hand-held Raman spectrometer for detection of the substance.

7. The device of claim 1, further comprising a control unit configured to operate the vibration engine.

8. The device of claim 1, wherein the vibration engine comprises a power source.

9. A method for detection of a substance by Raman spectroscopy, the method comprising:
    providing a device, which comprises a holder with an area configured for receiving a sample of the substance and a vibration engine configured for moving the holder,
    providing a SERS surface and arranging the SERS surface at the area of the holder,
    arranging a sample of the substance at the area,
    arranging the holder in front of a focusing lens of a spectrometer, where the area of the holder is facing the focusing lens of the spectrometer,
    starting the vibration engine by a control unit to move the holder in a three-dimensional motion to provide a large sampling area and hence to achieve a strong signal for detection of the substance, and wherein the holder is rotated around an axis perpendicularly through the area and is translated along the axis, and activating a spectrometer for detection mode.

10. The method of claim 9, wherein the spectrometer is a hand-held Raman spectrometer for detection of the substance.

11. The method of claim 9, further comprising:
    arranging a sample of the substance at the SERS surface.

12. The method of claim 9, further comprising:
    providing a vial containing a solvent,
    adding a sample of the substance to the solvent,
    closing the vial with a cap and shaking the vial until the substance has dissolved, and
    supplying a drop of the dissolved substance to the SERS surface.

13. The method of claim 12, wherein the substance is heroin.

14. The method of claim 12, wherein the substance is a narcotic substance, including at least one of amphetamine, alprazolam, cocaine, fentanyl, ketamine, MDMA, or methamphetamine.

15. The device of claim 2, comprising a hand-held Raman spectrometer for detection of the substance.

* * * * *